United States Patent
Fauran et al.

[11] 3,962,256
[45] June 8, 1976

[54] 2-AMINOMETHYL BENZIMIDAZOLE DERIVATIVES

[75] Inventors: Claude P. Fauran, Paris; Jeannine A. Eberlé, Chatou; Guy M. Raynaud; Nicole A. M. Dorme, both of Paris, all of France

[73] Assignee: Delalande S.A., Courbevoie, France

[22] Filed: June 20, 1974

[21] Appl. No.: 481,273

[30] Foreign Application Priority Data
July 3, 1973  France .................. 73.24388

[52] U.S. Cl. .................. 260/293.6; 260/247.5 EP; 260/309.2; 424/248; 424/267; 424/273
[51] Int. Cl.² .................. C07D 401/06
[58] Field of Search .............. 260/247.5 EP, 293.6, 260/309.2

[56] References Cited
UNITED STATES PATENTS
3,758,459  9/1973  Fauran et al. .................. 260/240 K FOREIGN PATENTS OR APPLICATIONS
1,470,319  10/1969  Germany Primary Examiner—G. Thomas Todd
Attorney, Agent, or Firm—Woodhams, Blanchard and Flynn

[57] ABSTRACT

Compounds having the formula

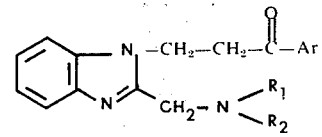

wherein Ar is phenyl optionally substituted by one or more halogens, alkyl having 1 to 4 carbons or alkoxy containing up to 4 carbons, and $R_1$ and $R_2$ each is alkyl having one to 4 carbons or

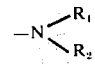

is piperidino, pyrrolidino, morpholino and hexamethyleneimino. The compounds are prepared by reacting the corresponding 2-chloromethyl benzimidazole with

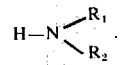

The compounds possess analgesic, antihypertensive, gastric antisecretory, antiinflammatory, antibronchoconstrictive, anticholinergic, spasmolytic, sedative, antiulcerous, vasodilatatory, central nervous system stimulant, antiarythmic, diuretic and antihistaminic properties.

7 Claims, No Drawings

2-AMINOMETHYL BENZIMIDAZOLE DERIVATIVES

The present invention relates to novel derivatives of 2-aminomethyl benzimidazole, their process of preparation and their therapeutic application.

The novel compounds according to the present invention correspond to the general formula:

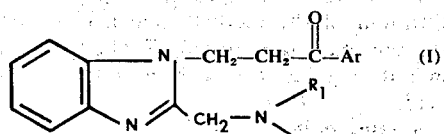

in which:
Ar represents a phenyl ring optionally substituted by one or more halogen atoms, by one or more alkyl radicals containing from 1 to 4 carbon atoms or by one or more alkoxy groups which each contain up to 4 carbon atoms; and $R_1$ and $R_2$ each represent an alkyl radical containing from 1 to 4 carbon atoms, or form together with the nitrogen atom to which they are attached, a heterocyclic radical selected from piperidino, pyrrolidino, morpholino and hexamethyleneimino.

The process according to the present invention comprises condensing a derivative of 2-chloromethyl benzimidazole of the general formula:

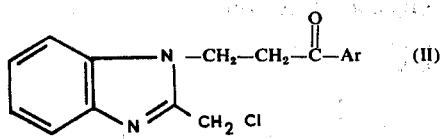

with an amine of the general formula:

in which the symbols, $R_1$, $R_2$ and Ar have the same significance as in formula (I).

The derivatives of formula (II) are themselves obtained by the reaction of a derivative of 2-hydroxymethyl benzimidazole of the general formula:

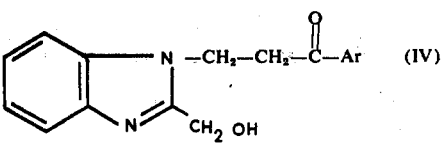

in which Ar has the same significance as in formula (I), with thionyl chloride of formula:

$$SOCl_2 \qquad (V)$$

the derivatives of formula (IV) resulting from the reaction, in a hydroalcoholic medium maintained under reflux, of the hydrochloride of a derivative of piperidinomethylacetophenone of the general formula:

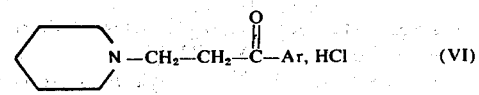

in which Ar has the same significance as in formula (I), with 2-methanol benzimidazole of formula:

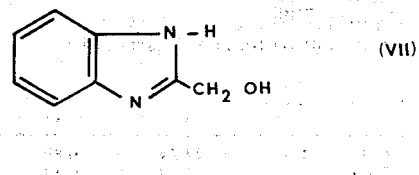

The following preparations are given by way of example to illustrate the present invention.

EXAMPLE 1

1-(2'-benzoylethyl)-2-dimethylaminomethyl benzimidazole (Code No: 72 522)

1st stage: 1-(benzoylethyl)-2-hydroxymethyl benzimidazole (Code No: 72 337)

A mixture of 0.06 mol of 2-hydroxymethyl benzimidazole, 0.06 mol of piperidinomethyl acetophenone hydrochloride, 48 ml. of methanol and 72 ml of water is maintained under reflux for 2 hours. After cooling to ambient temperature, the desired compound precipitates out, is filtered and recrystallised from 30 ml. of ethanol.

Melting point = 149°C
Yield = 66%
Empirical formula = $C_{17}H_{16}N_2O_2$

Elementary analysis:

|  | C | H | N |
|---|---|---|---|
| Calculated % | 72.84 | 5.75 | 9.99 |
| Found % | 72.68 | 5.85 | 10.00 |

2nd stage: 1-(2'-benzoylethyl)-2-chloromethyl benzimidazole (Code No: 72 370)

A solution of 0.95 mol of thionyl chloride in 270 c.c. of chloroform is added, at 15°C over a period of 1 hour, to a suspension of 0.62 mol of 1-(2'-benzoylethyl)-2-methanol benzimidazole in 480 c.c. of chloroform. After contact for 2 hours at ambient temperature, the excess thionyl chloride is evaporated and the methanolic solution of hydrochloride is neutralised with sodium bicarbonate. After filtration and evaporation, the crude base is recrystallised from ethyl acetate.

Melting point = 109°C
Yield = 67%
Empirical formula = $C_{17}H_{15}ClN_2O$

Elementary analysis:

|  | C | H | N |
|---|---|---|---|
| Calculated % | 68.34 | 5.06 | 9.38 |
| Found % | 68.14 | 5.18 | 9.24 |

3rd stage: 1-(2'-benzoylethyl)-2-dimethylaminomethyl benzimidazole (Code No. 72 522)

0.13 mol of 1-(2'-benzoylethyl)-2-chloromethyl benzimidazole obtained from the preceding stage and 0.26 mol of dimethylamine are dissolved in 300 c.c. of benzene.

The solution is maintained at 50°C for 3 hours. After cooling the dimethylamine hydrochloride formed is filtered off, and the benzene is evaporated. The base is crystallised from petroleum ether.

Melting point = 90°C
Yield = 70%
Empirical formula = $C_{19}H_{21}N_3O$

Elementary analysis:

|  | C | H | N |
|---|---|---|---|
| Calculated % | 74.24 | 6.89 | 13.67 |
| Found % | 74.18 | 6.87 | 13.52 |

EXAMPLE 2

1-(2'-benzoylethyl maleate)-2-diethylaminomethyl benzimidazole (Code No. 72 573)

0.1 mol. of 1-(2'-benzolyethyl)-2-chloromethyl benzimidazole obtained by the procedure of stage 2 according to Example 1, and 0.2 mol. of diethylamine are dissolved in 300 c.c. of benzene.

The solution is maintained at 40°C for 3 hours. After filtration of the diethylamine hydrochloride formed, the benzene is evaporated off. The crude base is salified in 200 c.c. of acetone with the aid of 0.1 mol. of maleic acid.

Melting point = 108°C
Yield = 43%
Empirical formula = $C_{25}H_{29}N_3O_5$

Elementary analysis:

|  | C | H | N |
|---|---|---|---|
| Calculated % | 66.50 | 6.47 | 9.31 |
| Found % | 66.50 | 6.55 | 9.51 |

The compounds listed in the following Table I have been prepared by the method of operation of the first stage according to Example 1, whilst the compounds listed in Table II have been prepared by the method of operation of stage 3 according to Example 1 or by the method of operation of Example 2, following the synthesis of the crude base, or its salt.

TABLE I

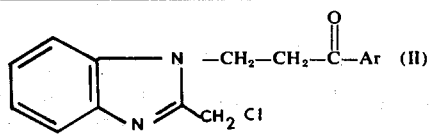

(II)

| Code No. | Ar. | Empirical Formula | Molecular Weight | Melting point (°C) | Yield % | Calculated % C | Calculated % H | Calculated % N | Found % C | Found % H | Found % N |
|---|---|---|---|---|---|---|---|---|---|---|---|
| 72316 | —C₆H₄—Cl | $C_{17}H_{14}Cl_2N_2O$ | 333.21 | 130 | 80 | 61.27 | 4.24 | 8.41 | 61.03 | 4.28 | 8.21 |
| 72336 | —C₆H₄—F | $C_{17}H_{14}ClFN_2O$ | 316.75 | 118 | 42 | 64.46 | 4.46 | 8.84 | 64.20 | 4.46 | 8.70 |
| 72411 | —C₆H₄—OC₄H₉(n) | $C_{21}H_{23}ClN_2O_2$ | 370.87 | 80 | 58 | 68.01 | 6.25 | 7.55 | 68.00 | 6.27 | 7.47 |
| 72294 | —C₆H₄—CH₃ | $C_{18}H_{17}ClN_2O$ | 312.78 | 139 | 51 | 69.11 | 5.48 | 8.96 | 69.03 | 5.60 | 8.85 |
| 72335 | —C₆H₃(CH₃)₂ | $C_{19}H_{19}ClN_2O$ | 326.81 | 90 | 57 | 69.82 | 5.86 | 8.57 | 69.99 | 5.85 | 8.43 |
| 72346 | —C₆H₃(OCH₃)₂ | $C_{19}H_{19}ClN_2O_3$ | 358.81 | 138 | 60 | 63.60 | 5.34 | 7.81 | 63.45 | 5.57 | 7.61 |
| 72379 | —C₆H₂(OCH₃)₃ | $C_{20}H_{21}ClN_2O_4$ | 388.84 | 135 | 50 | 61.77 | 5.44 | 7.21 | 61.97 | 5.39 | 7.07 |

TABLE II

| Code No. | Ar. | -N(R1)(R2) | Form | Empirical Formula | Molecular weight | Melting point (°C) | Yield (%) | Elementary Analysis | C | H | N |
|---|---|---|---|---|---|---|---|---|---|---|---|
| 72493 | -C₆H₅ | -N(pyrrolidine) | base | C₂₁H₂₃N₃O | 333.42 | 97 | 74 | % Calculated Found | 75.64 75.79 | 6.95 7.04 | 12.60 12.41 |
| 72491 | -C₆H₅ | -N(piperidine) | base | C₂₂H₂₅N₃O | 347.44 | 136 | 53 | Calculated Found | 76.05 75.98 | 7.25 7.28 | 12.10 12.13 |
| 72494 | -C₆H₅ | -N(morpholine) | base | C₂₁H₂₃N₃O₂ | 349.42 | 111 | 71 | Calculated Found | 72.18 72.00 | 6.64 6.57 | 6.57 12.07 |
| 72451 | -C₆H₅ | -N(hexamethyleneimine) | base | C₂₃H₂₇N₃O | 358.45 | 110 | 58 | Calculated Found | 76.42 76.23 | 7.53 7.58 | 11.63 11.83 |
| 72479 | -C₆H₄-Cl | N(CH₃)₂ | base | C₁₉H₂₀ClN₃O | 341.83 | 123 | 65 | Calculated Found | 66.76 66.76 | 5.90 5.75 | 12.29 12.12 |
| 72390 | -C₆H₄-Cl | N(C₂H₅)₂ | base | C₂₁H₂₄ClN₃O | 369.88 | 111 | 67 | Calculated Found | 68.19 68.36 | 6.54 6.65 | 11.36 11.43 |
| 72366 | -C₆H₄-Cl | -N(pyrrolidine) | base | C₂₁H₂₂ClN₃O | 367.87 | 135 | 73 | % Calculated Found | 68.56 68.57 | 6.03 6.16 | 11.42 11.47 |
| 72389 | -C₆H₄-Cl | -N(piperidine) | base | C₂₂H₂₄ClN₃O | 381.89 | 156 | 57 | Calculated Found | 69.19 68.99 | 6.33 6.26 | 11.00 11.01 |
| 72359 | -C₆H₄-Cl | -N(morpholine) | base | C₂₁H₂₂ClN₃O₂ | 383.87 | 131 | 78 | Calculated Found | 65.70 65.63 | 5.78 5.77 | 10.95 10.80 |
| 72418 | -C₆H₄-Cl | -N(hexamethyleneimine) | base | C₂₃H₂₆ClN₃O | 395.92 | 121 | 30 | Calculated Found | 69.77 69.83 | 6.62 6.44 | 10.61 10.49 |
| 72663 | -C₆H₄-F | -N(CH₃)₂ | maleate | C₂₃H₂₄FN₃O₅ | 441.45 | 152 | 50 | Calculated Found | 62.57 62.44 | 5.48 5.58 | 9.52 9.57 |
| 72568 | -C₆H₄-F | -N(C₂H₅)₂ | maleate | C₂₅H₂₈FN₃O₅ | 469.50 | 130 | 32 | Calculated Found | 63.95 63.75 | 6.01 6.08 | 8.95 8.83 |
| 72708 | -C₆H₄-F | -N(pyrrolidine) | base | C₂₁H₂₂FN₃O | 351.41 | 81 | 77 | Calculated Found | 71.77 71.80 | 6.31 6.46 | 11.96 11.84 |
| 72487 | -C₆H₄-F | -N(piperidine) | base | C₂₂H₂₄FN₃O | 365.44 | 114 | 71 | Calculated Found | 72.30 72.28 | 6.62 6.68 | 11.50 11.47 |
| 72526 | -C₆H₄-F | -N(morpholine) | maleate | C₂₅H₂₆FN₃O₆ | 483.48 | 135 | 61 | Calculated Found | 62.10 62.20 | 5.42 5.43 | 8.69 8.88 |
| 72488 | -C₆H₄-F | -N(hexamethyleneimine) | base | C₂₃H₂₆FN₃O | 379.46 | 104 | 68 | Calculated Found | 72.80 72.79 | 6.91 7.03 | 11.07 10.98 |
| 72524 | -C₆H₄-OC₄H₉ (n) | -N(CH₃)₂ | base | C₂₃H₂₉N₃O₂ | 379.49 | 84 | 86 | Calculated Found | 72.79 72.68 | 7.70 7.63 | 11.07 10.94 |

TABLE II-continued

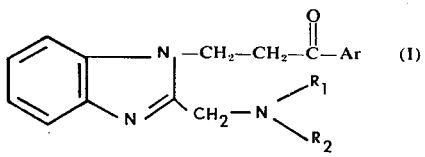

| Code No. | Ar. | —N<R₁/R₂ | Form | Empirical Formula | Molecular weight | Melting point (°C) | Yield (%) | Elementary Analysis | | C | H | N |
|---|---|---|---|---|---|---|---|---|---|---|---|---|
| 72727 | —⟨⟩—OC₄H₉ (n) | —N(C₂H₅)₂ | base | $C_{25}H_{33}N_3O_2$ | 407.54 | 84 | 50 | Calculated Found | | 73.67 73.46 | 8.16 8.16 | 10.31 10.23 |
| 72465 | —⟨⟩—OC₄H₉ (n) | -N⟨⟩ | base | $C_{25}H_{31}N_3O_2$ | 405.52 | 113 | 69 | Calculated Found | | 74.04 74.14 | 7.71 7.73 | 10.36 10.52 |
| 72464 | —⟨⟩—OC₄H₉ (n) | -N⟨⟩ | base | $C_{26}H_{33}N_3O_2$ | 419.55 | 130 | 73 | Calculated Found | | 74.43 74.23 | 7.93 7.80 | 10.02 10.19 |
| 72523 | —⟨⟩—OC₄H₉ (n) | -N⟨⟩O | base | $C_{25}H_{31}N_3O_3$ | 421.52 | 127 | 72 | % Calculated Found | | 71.23 71.15 | 7.41 7.27 | 9.97 10.11 |
| 72463 | —⟨⟩—OC₄H₉ (n) | -N⟨⟩ | base | $C_{27}H_{35}N_3O_2$ | 433.57 | 100 | 60 | Calculated Found | | 74.79 74.94 | 8.14 8.25 | 9.69 9.89 |
| 72457 | —⟨⟩—CH₃ | —N(CH₃)₂ | base | $C_{20}H_{23}N_3O$ | 321.41 | 106 | 75 | Calculated Found | | 74.73 74.82 | 7.21 7.21 | 13.07 12.87 |
| 72574 | —⟨⟩—CH₃ | —N(C₂H₅)₂ | maleate | $C_{26}H_{31}N_3O_5$ | 465.53 | 99 | 55 | Calculated Found | | 67.08 66.90 | 6.71 6.81 | 9.03 9.03 |
| 72476 | —⟨⟩—CH₃ | -N⟨⟩ | base | $C_{22}H_{25}N_3O$ | 347.44 | 122 | 63 | Calculated Found | | 76.05 75.89 | 7.25 7.14 | 12.10 12.03 |
| 72477 | —⟨⟩—CH₃ | -N⟨⟩ | base | $C_{23}H_{27}N_3O$ | 361.47 | 155 | 82 | Calculated Found | | 76.42 76.21 | 7.53 7.33 | 11.63 11.44 |
| 72478 | —⟨⟩—CH₃ | -N⟨⟩O | base | $C_{22}H_{25}N_3O_2$ | 363.44 | 135 | 70 | Calculated Found | | 72.70 72.70 | 6.93 6.79 | 11.56 11.50 |
| 72483 | —⟨⟩—CH₃ | -N⟨⟩ | base | $C_{24}H_{29}N_3O$ | 375.50 | 99 | 56 | % Calculated Found | | 76.76 76.61 | 7.78 7.85 | 11.19 11.13 |
| 72712 | —⟨⟩—CH₃ (H₃C-) | —N(CH₃)₂ | base | $C_{21}H_{25}N_3O$ | 335.43 | 135 | 54 | Calculated Found | | 75.19 75.24 | 7.51 7.50 | 12.53 12.44 |
| 72736 | —⟨⟩—CH₃ (H₃C-) | —N(C₂H₅)₂ | maleate | $C_{27}H_{33}N_3O_5$ | 479.56 | 107 | 48 | Calculated Found | | 67.62 67.65 | 6.94 7.00 | 8.76 8.68 |
| 72446 | —⟨⟩—CH₃ (H₃C-) | -N⟨⟩ | base | $C_{23}H_{27}N_3O$ | 361.47 | 118 | 63 | Calculated Found | | 76.42 76.62 | 7.53 7.58 | 11.63 11.45 |

TABLE II-continued

| Code No. | Ar. | $-N\begin{smallmatrix}R_1\\R_2\end{smallmatrix}$ | Form | Empirical Formula | Molecular weight | Melting point (°C) | Yield (%) | Elementary Analysis | C | H | N |
|---|---|---|---|---|---|---|---|---|---|---|---|
| 72540 |  |  | base | $C_{24}H_{29}N_3O$ | 375.50 | 132 | 76 | Calculated<br>Found | 76.76<br>76.86 | 7.78<br>7.79 | 11.19<br>11.27 |
| 72447 |  |  | base | $C_{23}H_{27}N_3O_2$ | 377.47 | 116 | 53 | Calculated<br>Found | 73.18<br>73.04 | 7.21<br>7.23 | 11.13<br>11.06 |
| 72603 |  |  | base | $C_{25}H_{31}N_3O \cdot \tfrac{3}{4}H_2O$ | 403.04 | 72 | 46 | Calculated<br>Found | 74.50<br>74.44 | 8.28<br>8.19 | 10.43<br>10.55 |
| 72490 |  | $-N(CH_3)_2$ | base | $C_{21}H_{25}N_3O_3$ | 367.40 | 95 | 76 | %<br>Calculated<br>Found | 68.64<br>68.67 | 6.86<br>6.88 | 11.44<br>11.24 |
| 72692 |  | $-N(C_2H_5)_2$ | maleate | $C_{27}H_{33}N_3O_7$ | 511.56 | 123 | 41 | Calculated<br>Found | 63.39<br>63.19 | 6.50<br>6.54 | 8.21<br>8.26 |
| 72617 |  |  | base | $C_{23}H_{27}N_3O_3$ | 393.47 | 82 | 60 | Calculated<br>Found | 70.20<br>70.00 | 6.92<br>7.01 | 10.68<br>10.58 |
| 72377 |  |  | base | $C_{24}H_{29}N_3O_3$ | 407.49 | 101 | 85 | Calculated<br>Found | 70.73<br>70.93 | 7.17<br>7.29 | 10.31<br>10.19 |
| 72391 |  |  | base | $C_{23}H_{27}N_3O_4$ | 409.47 | 150 | 65 | Calculated<br>Found | 67.46<br>67.47 | 6.65<br>6.68 | 10.26<br>10.14 |
| 72398 |  |  | base | $C_{25}H_{31}N_3O_3$ | 421.52 | 100 | 57 | Calculated<br>Found | 71.23<br>71.04 | 7.41<br>7.47 | 9.97<br>9.81 |

TABLE II-continued

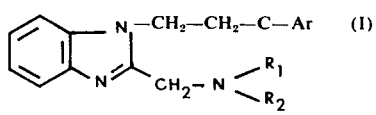

| Code No. | Ar. | $-N\begin{smallmatrix}R_1\\R_2\end{smallmatrix}$ | Form | Empirical Formula | Molecular weight | Melting point (°C) | Yield (%) | | Elementary Analysis | | |
|---|---|---|---|---|---|---|---|---|---|---|---|
| | | | | | | | | | C | H | N |
| 72534 | 3,4,5-tri-OCH₃-phenyl | —N(CH₃)₂ | base | $C_{22}H_{27}N_3O_4$ | 397.46 | 164 | 86 | Calculated | 64.48 | 6.85 | 10.57 |
| | | | | | | | | Found | 66.26 | 6.87 | 10.51 |
| 72539 | 3,4,5-tri-OCH₃-phenyl | —N(C₂H₅)₂ | base | $C_{24}H_{31}N_3O_4$ | 425.51 | 167 | 50 | % Calculated | 67.74 | 7.34 | 9.88 |
| | | | | | | | | Found | 67.91 | 7.28 | 9.97 |
| 72414 | 3,4,5-tri-OCH₃-phenyl | —N(pyrrolidinyl) | base | $C_{24}H_{29}N_3O_4$ | 423.50 | 154 | 71 | Calculated | 68.06 | 6.90 | 9.92 |
| | | | | | | | | Found | 67.86 | 6.92 | 9.75 |
| 72413 | 3,4,5-tri-OCH₃-phenyl | —N(piperidinyl) | base | $C_{25}H_{31}N_3O_4$ | 437.52 | 143 | 60 | Calculated | 68.63 | 7.14 | 9.61 |
| | | | | | | | | Found | 68.43 | 7.06 | 9.45 |
| 72525 | 3,4,5-tri-OCH₃-phenyl | —N(morpholinyl) | maleate | $C_{28}H_{33}N_3O_9$ | 555.57 | 154 | 74 | Calculated | 60.53 | 5.99 | 7.56 |
| | | | | | | | | Found | 60.72 | 5.89 | 7.63 |
| 72412 | 3,4,5-tri-OCH₃-phenyl | —N(hexamethyleneimino) | base | $C_{26}H_{33}N_3O_4$ | 451.55 | 136 | 55 | Calculated | 69.15 | 7.37 | 9.31 |
| | | | | | | | | Found | 69.35 | 7.48 | 9.11 |

The compounds of formula (I) have been tested on animals in the laboratory and have been shown to possess analgesic, antihypertensive, gastric antisecretory, anti-inflammatory, antibronochoconstrictive and anticholinergic, spasmolytic, sedative, antiulcerous, vasodilatatory, stimulants for the central nervous system, antiarythmic, diuretic and antihistaminic properties.

1. Analgesic properties

The compounds of formula (I), administered by oral means to the mouse, are capable of reducing the number of painful stretchings caused by the intraperitoneal injection of acetic acid.

By way of example, the following Table III lists the results obtained by administration of 100 mg/Kg/p.o. of different compounds of formula (I).

TABLE III

| Code No. of compound tested | Percentage reduction of number of painful stretchings - (%) |
| --- | --- |
| 72 491 | 65 |
| 72 523 | 45 |
| 72 391 | 60 |
| 72 617 | 70 |
| 72 487 | 80 |
| 72 663 | 60 |
| 72 603 | 50 |
| 72 708 | 60 |
| 72 574 | 45 |

2. Antihypertensive properties

The compounds of formula (I), administered by oral means to a rat suffering from high blood pressure, are capable of lowering the systolic arteriel pressure.

By way of example, there is provided in the following Table IV the results obtained by administration of different compounds of formula (I).

TABLE IV

| Code No. of compound tested | Dose administered (mg/Kg/p.o.) | Percentage of rats with high blood pressure whose systolic arteriel pressure is returned to normal (%) |
| --- | --- | --- |
| 72 491 | 200 | 50 |
| 72 414 | 150 | 75 |
| 72 525 | 200 | 50 |
| 72 526 | 100 | 75 |
| 72 568 | 200 | 50 |
| 72 479 | 200 | 50 |
| 72 457 | 200 | 50 |

3. Gastric antisecretory properties

Administered by intraduodenal means to a rat, the compounds of formula (I) are capable of reducing the gastric secretion measured after Shay ligature.

By way of example, the following Table V gives the results obtained by administration of 50 mg/Kg/i.d. of different compounds of formula (I).

TABLE V

| Code No. of compound tested | Percentage reductions in volume of gastric secretion - (%) |
| --- | --- |
| 72 493 | 25 |
| 72 494 | 25 |
| 72 523 | 25 |
| 72 487 | 40 |

4. Antiinflammatory properties

These properties are shown by a diminution of the local oedema caused by the sub-plantar injection of a phlogogenic agent, such as carraghenin, in the rat following the oral administration of compounds of formula (I).

The following Table VI lists, by way of example, the percentage reduction of the oedems caused by the sub-plantar injection of carraghenin, resulting from the administration of 100 mg/Kg/p.o. of different compounds of formula (I).

TABLE VI

| Code No. of compound tested | Percentage reduction of sub-plantar oedema (%) |
| --- | --- |
| 72 494 | 40 |
| 72 488 | 50 |

TABLE VI-continued

| Code No. of compound tested | Percentage reduction of sub-plantar oedema (%) |
| --- | --- |
| 72 526 | 55 |
| 72 447 | 40 |
| 72 366 | 60 |
| 72 712 | 70 |
| 72 390 | 60 |

5. Antibronchoconstrictive and anticholinergic properties.

Injected by intraveinous or intraduodenal means, the compounds of formula (I) are capable of opposing the bronchoconstriction provoked in the guinea-pig by the itraveinous injection of acetylcholine by the Konzett method.

By way of example, the following Table VII lists the results obtained by the administration of different compounds of formula (I)

TABLE VII

| Code No. of compound tested | Dose Administered | Percentage inhibition of bronchoconstriction (%) |
| --- | --- | --- |
| 72 573 | 5 mg/kg/i.v. | 100 |
| 72 412 | 100 mg/kg/i.d. | 80 |
| 72 414 | 100 mg/kg/i.d. | 50 |
| 72 525 | 100 mg/kg/i.d. | 80 |
| 72 534 | 100 mg/kg/i.d. | 50 |
| 72 391 | 100 mg/kg/i.d. | 100 |
| 72 398 | 100 mg/kg/i.d. | 100 |
| 72 487 | 100 mg/kg/i.d. | 60 |
| 72 526 | 100 mg/kg/i.d. | 75 |
| 72 447 | 100 mg/kg/i.d. | 50 |
| 72 540 | 100 mg/kg/i.d. | 50 |
| 72 603 | 100 mg/kg/i.d. | 50 |
| 72 708 | 100 mg/kg/i.d. | 90 |
| 72 457 | 100 mg/kg/i.d. | 80 |
| 72 736 | 10 mg/kg/i.v. | 90 |
| 72 727 | 100 mg/kg/i.d. | 100 |

6. Spasmolytic properties

The compounds of formula (I), introduced in the conserving medium are capable of opposing the contractural action of barium chloride on the isolated duodenum of the rat. This activity is evaluated by taking papaverine as standard.

Thus, the compounds of Code Nos. 72 573, 72 708, and 72 736 presents an equivalent spasmolytic actvity to that of papaverine.

7. Sedative properties

The compounds of formula (I), administered by oral means to the mouse, reduce the number of explorations in the escape enclosure.

By way of example, the following Table VIII lists the results obtained by the administration of 100 mg/Kg/p.o. of different compounds of formula (I).

TABLE VIII

| Code No. of compound tested | Percentage reduction of number of explorations in the escape enclosure (%) |
| --- | --- |
| 72 464 | 30 |
| 72 377 | 30 |
| 72 391 | 50 |
| 72 663 | 30 |
| 72 540 | 30 |
| 72 603 | 30 |
| 72 712 | 40 |
| 72 692 | 30 |

8. Antiulcerous properties

The compounds of formula (I) administered by intraduodenal means reduce the extent of gastric ulcers, provoked in a rat by tying of the pylorus (Shay ulcers).

By way of example, there is listed in the following Table IX, the results obtained by the administrations of 50 mg/Kg/i.d. of different compounds of formula (I).

TABLE IX

| Code No. of compound tested | Percentage reduction of Shay ulcers - (%) |
| --- | --- |
| 72 377 | 55 |
| 72 398 | 25 |
| 72 490 | 30 |
| 72 488 | 25 |
| 72 526 | 40 |
| 72 447 | 35 |
| 72 603 | 35 |
| 72 359 | 35 |
| 72 366 | 40 |
| 72 712 | 55 |
| 72 708 | 30 |
| 72 390 | 40 |
| 72 479 | 30 |
| 72 457 | 30 |
| 72 574 | 45 |
| 72 736 | 30 |

9. Vasodilatatory properties

The compounds of formula (I) are capable of augmenting the flow of the coronary vessels of the isolated heart of a guinea-pig when said compounds are added in the perfusion liquid of said organ.

By way of example, there can be found in the following Table X, the percentage augmentation of the flow of the isolated heart of a guinea-pig by adding different compounds of formula (I) to the perfusion liquid, in a concentration of 1 μg/ml.

TABLE X

| Code No. of compound tested | Percentage augmentations of flow of isolated heart of a guinea-pig (%) |
| --- | --- |
| 72 490 | 140 |
| 72 479 | 80 |
| 72 478 | 50 |
| 72 692 | 60 |

10. Central nervous system stimulating properties

The compounds of formula (I), administered by oral means to the mouse, provoke an augmentation of the number of excursions into the escape enclosure.

Thus, following the administration of 100 mg/Kg/p.o. of the compounds of Code Nos. 72 457 and 72 736, an augmentation of 30% in the number of excursions in the escape test, is observed.

11. Antiarythmic properties

Administered by intraperitoneal means, the compounds of formula (I) are capable of protecting the mouse against the ventricular fibrillations provoked by the inhalation of chloroform.

By way of example, the compounds of Code Nos. 72 488, 72 568 and 72 479 present a DE 50 of 200 mg/Kg/i.p.

12. Diuretic properties

The compounds of formula (I), administered by oral means to the mouse, simultaneously with a volume of 1 ml. of an isotonic solution of sodium chloride per 25 g of the corporeal weight of the mouse, are capable of provoking an augmentation of the volume of urine emitted by reference to control animals, the volume being measured for 6 hours following administration.

By way of example, the following Table XI lists the results obtained by the administration of 25 mg/Kg/p.o. of different compounds of formula (I).

TABLE XI

| Code No. of compound tested | Percentage augmentation of urinary elimination (%) |
| --- | --- |
| 72 447 | 70 |
| 72 603 | 45 |
| 72 457 | 45 |
| 72 692 | 70 |

13. Antihistaminic properties

The compounds of formula I, introduced in the conserving medium, are capable of opposing the contractural action of histamine on the isolated ileum of the guinea-pig. This activity is evaluated by taking promethazine as standard.

By way of example, the compound of Code No. 72 366 presents an equivalent activity to that of promethazine.

As a result of a comparison between the pharmacologically active doses mentioned above and the lethal doses listed in the following Table XII, the difference between said doses is sufficiently great to permit the utilisation of the compounds of formula (I) in therapeutics.

TABLE XII

| Code No. of compound tested | Dose administered (mg/Kg/p.o.) | Percentage mortality (%) |
| --- | --- | --- |
| 72 491 | 2 000 | 0 |
| 72 493 | 2 200 | ≈50 |
| 72 573 | 1 250 | ≈50 |
| 72 494 | 2 000 | 0 |
| 72 464 | 2 000 | 0 |
| 72 523 | 2 000 | 0 |
| 72 412 | 2 000 | 0 |
| 72 414 | 1 800 | ≈50 |
| 72 525 | 2 000 | ≈10 |
| 72 534 | 2 000 | 0 |
| 72 377 | 2 000 | 0 |
| 72 391 | 2 000 | 0 |
| 72 398 | 2 000 | 0 |
| 72 490 | 1 800 | ≈50 |
| 72 617 | 2 600 | ≈50 |
| 72 487 | 1 825 | ≈50 |
| 72 488 | 2 000 | 0 |
| 72 526 | 1 400 | ≈50 |
| 72 568 | 1 425 | ≈50 |
| 72 663 | 1 800 | ≈50 |
| 72 447 | 2 000 | 0 |
| 72 540 | 2 000 | 0 |
| 72 603 | 2 000 | 0 |
| 72 359 | 2 000 | 0 |
| 72 366 | 2 000 | 0 |
| 72 712 | 2 000 | 0 |
| 72 708 | 1 600 | ≈50 |
| 72 390 | 2 000 | 0 |
| 72 479 | 2 000 | 0 |
| 72 457 | 2 000 | 0 |
| 72 478 | 2 000 | 0 |
| 72 574 | 2 200 | ≈50 |
| 72 692 | 1 400 | ≈50 |
| 72 736 | 2 000 | ≈10 |
| 72 727 | 2 000 | 0 |

The compounds of formula (I) are useful in the treatment of gastro-duodenal ulcers, visceral spasms, asthma, anxiety, nervousness, painful inflammations, diverse originating pains, circulatory insufficiencies, cardiac arythmies, hypertension, oedemas, allergies and asthenia.

They may be administered by oral means in the form of tablets, gelules and dragees containing 10 to 400 mg of active ingredient (1 to 6 times per day), or suspensions containing 0.5 to 5% of active ingredient (1 to 6 spoonfuls per day), by parenteral means in the form of injectable ampoules containing 5 to 50 mg of active ingredient (1 to 3 times per day) and by rectal means in the form of suppositories containing 10 to 200 mg of active ingredient (1 to 3 times per day).

Accordingly, the present invention also relates to a therapeutic composition comprising a compound of the general formula (I) together with a therapeutically acceptable carrier.

What we claim is:

1. A compound having the formula

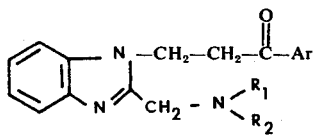

wherein Ar is phenyl or phenyl substituted by one halogen, or one or two alkyl having 1 to 4 carbon atoms, or one, two or three alkoxy having 1 to 4 carbon atoms, and $R_1$ and $R_2$ each is alkyl having one to 4 carbon atoms or

is piperidino, pyrrolidino, morpholino or hexamethyleneimino, and the pharmacologically acceptable acid addition salts thereof.

2. A compound as claimed in claim 1, in which Ar is phenyl.

3. A compound as claimed in claim 1, in which Ar is p-chlorophenyl or p-fluorophenyl.

4. A compound as claimed in claim 1, in which Ar is p-tolyl or 2,4-dimethyl phenyl.

5. A compound as claimed in claim 1, in which Ar is p-(n-butoxy)phenyl, 2,4-dimethoxyphenyl or 3,4,5-trimethoxyphenyl.

6. A compound as claimed in claim 1 in which

is dimethylamino, diethylamino, pyrrolidino, piperidino, morpholino or hexamethyleneimino.

7. A compound as claimed in claim 1, in which Ar is 2,4-dimethylphenyl and

is piperidino.

* * * * *